(12) United States Patent
Dunn et al.

(10) Patent No.: US 12,201,396 B2
(45) Date of Patent: Jan. 21, 2025

(54) OPTICAL SPECKLE RECEIVER

(71) Applicant: ROCKLEY PHOTONICS LIMITED, Altrincham (GB)

(72) Inventors: Cody Dunn, Costa Mesa, CA (US); Kate LeeAnn Bechtel, Pleasant Hill, CA (US)

(73) Assignee: Rockley Photonics Limited, Altrincham (GB)

( * ) Notice: Subject to any disclaimer, the term of this patent is extended or adjusted under 35 U.S.C. 154(b) by 0 days.

(21) Appl. No.: 17/822,419

(22) Filed: Aug. 25, 2022

(65) Prior Publication Data
US 2023/0087295 A1    Mar. 23, 2023

Related U.S. Application Data

(63) Continuation of application No. 17/703,920, filed on Mar. 24, 2022, now Pat. No. 12,109,006.
(Continued)

(51) Int. Cl.
A61B 5/00      (2006.01)
G02B 3/00      (2006.01)
(Continued)

(52) U.S. Cl.
CPC .......... A61B 5/0028 (2013.01); G02B 3/0006 (2013.01); A61B 5/0261 (2013.01);
(Continued)

(58) Field of Classification Search
CPC ... A61B 5/0028; A61B 5/0261; A61B 5/0295; A61B 5/681; A61B 2562/0233; G02B 3/0006
(Continued)

(56) References Cited

U.S. PATENT DOCUMENTS 4,674,011 A *  6/1987  Patton .................... G02B 6/262
                                              362/334
5,497,769 A *  3/1996  Gratton .................. G01N 21/49
                                              600/323
(Continued)

FOREIGN PATENT DOCUMENTS

CA    2 861 089 C    1/2021
CN    110301896 B    10/2019
(Continued)

OTHER PUBLICATIONS

Bi, R. et al., "Fast pulsatile blood flow measurement in deep tissue through a multimode detection fiber", Journal of Biomedical Optics, May 13, 2020, pp. 055003-1 through 055003-10, vol. 25(5), SPIE.
(Continued)

Primary Examiner — Mohamed K Amara
(74) Attorney, Agent, or Firm — Lewis Roca Rothgerber Christie LLP

(57) ABSTRACT

An optical speckle receiver for receiving a speckle signal from a sample, the optical speckle receiver comprising an optical detector and an aperture and/or lens array. The aperture and array respectively comprise a plurality of apertures or lenses and is located between the sample and the optical detector such that the received speckle pattern is obtained from multiple discrete sample locations.

21 Claims, 15 Drawing Sheets

Related U.S. Application Data

(60) Provisional application No. 63/243,021, filed on Sep. 10, 2021.

(51) Int. Cl.
  *A61B 5/026* (2006.01)
  *A61B 5/0295* (2006.01)

(52) U.S. Cl.
  CPC ............. *A61B 5/0295* (2013.01); *A61B 5/681* (2013.01); *A61B 2562/0233* (2013.01)

(58) Field of Classification Search
  USPC .......................................................... 356/51
  See application file for complete search history.

(56) References Cited

U.S. PATENT DOCUMENTS

| | | | |
|---|---|---|---|
| 5,532,860 A | 7/1996 | Hershey et al. | |
| 5,772,587 A * | 6/1998 | Gratton | A61B 5/14552 |
| | | | 600/323 |
| 6,154,259 A * | 11/2000 | Hargis | H04N 9/3132 |
| | | | 353/69 |
| 6,243,601 B1 | 6/2001 | Wist | |
| 6,256,016 B1 * | 7/2001 | Piot | G06F 3/0317 |
| | | | 250/208.2 |
| 7,035,679 B2 | 4/2006 | Addison et al. | |
| 7,113,817 B1 | 9/2006 | Winchester, Jr. et al. | |
| 7,202,466 B2 * | 4/2007 | Babayoff | G02B 27/0933 |
| | | | 359/368 |
| 7,474,407 B2 * | 1/2009 | Gutin | A61B 5/0066 |
| | | | 356/479 |
| 7,616,984 B2 * | 11/2009 | Barbour | A61B 5/4312 |
| | | | 250/332 |
| 7,922,664 B2 | 4/2011 | Elliott | |
| 7,925,056 B2 | 4/2011 | Presura et al. | |
| 8,277,384 B2 | 10/2012 | Fine | |
| 8,313,439 B2 | 11/2012 | McCombie et al. | |
| 8,343,062 B2 | 1/2013 | Fortin et al. | |
| 8,343,063 B2 | 1/2013 | Borgos | |
| 8,398,556 B2 | 3/2013 | Sethi et al. | |
| 8,868,149 B2 | 10/2014 | Eisen et al. | |
| 8,920,332 B2 | 12/2014 | Hong et al. | |
| 8,945,017 B2 | 2/2015 | Venkatraman et al. | |
| 8,948,832 B2 | 2/2015 | Hong et al. | |
| 8,956,303 B2 | 2/2015 | Hong et al. | |
| 8,998,815 B2 | 4/2015 | Venkatraman et al. | |
| 9,005,129 B2 | 4/2015 | Venkatraman et al. | |
| 9,113,794 B2 | 8/2015 | Hong et al. | |
| 9,113,795 B2 | 8/2015 | Hong et al. | |
| 9,149,216 B1 | 10/2015 | Eisen et al. | |
| 9,155,480 B2 | 10/2015 | Thakor et al. | |
| 9,226,673 B2 | 1/2016 | Ferguson, Jr. et al. | |
| 9,237,855 B2 | 1/2016 | Hong et al. | |
| 9,307,917 B2 | 4/2016 | Hong et al. | |
| 9,687,162 B2 | 6/2017 | Vetter et al. | |
| 9,704,050 B2 | 7/2017 | Lee et al. | |
| 9,730,622 B2 | 8/2017 | Eisen et al. | |
| 9,848,787 B2 | 12/2017 | White et al. | |
| 9,851,298 B1 * | 12/2017 | Isikman | G01N 21/33 |
| 9,931,040 B2 | 4/2018 | Homyk et al. | |
| 9,970,955 B1 | 5/2018 | Homyk et al. | |
| 10,004,406 B2 | 6/2018 | Yuen et al. | |
| 10,058,256 B2 | 8/2018 | Chen et al. | |
| 10,178,959 B1 | 1/2019 | Homyk et al. | |
| 10,178,973 B2 | 1/2019 | Venkatraman et al. | |
| 10,194,808 B1 | 2/2019 | Thompson et al. | |
| 10,206,576 B2 | 2/2019 | Shcherbakov et al. | |
| 10,215,698 B2 | 2/2019 | Han et al. | |
| 10,349,825 B2 | 7/2019 | Kwon et al. | |
| 10,357,165 B2 | 7/2019 | Yoon | |
| 10,492,684 B2 | 12/2019 | Khachaturian et al. | |
| 10,506,926 B2 | 12/2019 | Khachaturian et al. | |
| 10,506,955 B2 | 12/2019 | Tholl et al. | |
| 10,568,527 B2 | 2/2020 | Yoon et al. | |
| 10,588,519 B2 | 3/2020 | Yuen et al. | |
| 10,602,987 B2 | 3/2020 | Khachaturian et al. | |
| 10,667,688 B2 | 6/2020 | Khachaturian et al. | |
| 10,681,259 B2 | 6/2020 | Ichiki et al. | |
| 10,681,283 B2 | 6/2020 | Nakashima et al. | |
| 10,694,997 B2 | 6/2020 | Kim et al. | |
| 10,722,177 B2 | 7/2020 | Homyk et al. | |
| 10,750,956 B2 | 8/2020 | Zalevsky et al. | |
| 10,813,597 B2 | 10/2020 | Rice et al. | |
| 10,820,858 B2 | 11/2020 | Yoon et al. | |
| 10,842,422 B2 | 11/2020 | Yu et al. | |
| 10,871,503 B1 | 12/2020 | Homyk et al. | |
| 10,895,525 B2 * | 1/2021 | Swanson | G01S 7/4817 |
| 10,966,616 B2 | 4/2021 | De Morree et al. | |
| 10,973,422 B2 | 4/2021 | Pantelopoulos et al. | |
| 11,096,601 B2 | 8/2021 | Hong et al. | |
| 11,129,544 B2 | 9/2021 | Zalevsky et al. | |
| 11,202,582 B2 | 12/2021 | Verkruijsse et al. | |
| 11,213,217 B2 | 1/2022 | Han et al. | |
| 11,278,220 B2 | 3/2022 | Tucker et al. | |
| 11,298,035 B2 | 4/2022 | Huijbregts et al. | |
| 11,369,275 B2 | 6/2022 | Song et al. | |
| 11,445,922 B2 | 9/2022 | Naima | |
| 11,553,851 B2 | 1/2023 | Kim et al. | |
| 11,583,185 B2 | 2/2023 | Homyk et al. | |
| 11,666,238 B2 | 6/2023 | Rege et al. | |
| 11,666,277 B2 | 6/2023 | Yoon et al. | |
| 11,684,281 B2 | 6/2023 | Pantelopoulos et al. | |
| 11,690,513 B2 | 7/2023 | Hu et al. | |
| 11,696,693 B2 | 7/2023 | Wong | |
| 11,709,120 B2 | 7/2023 | Rice et al. | |
| 11,744,491 B2 | 9/2023 | Dunn et al. | |
| 11,751,811 B2 | 9/2023 | Sun et al. | |
| 11,759,116 B2 | 9/2023 | White et al. | |
| 11,759,121 B2 | 9/2023 | Mccann et al. | |
| 11,771,343 B2 | 10/2023 | Sacha | |
| 11,800,990 B2 | 10/2023 | White et al. | |
| 11,857,301 B1 | 1/2024 | Homyk et al. | |
| 11,883,134 B2 | 1/2024 | Leabman | |
| 11,890,081 B2 | 2/2024 | Jang | |
| 11,980,451 B2 | 5/2024 | Albert | |
| 2002/0195496 A1 * | 12/2002 | Tsikos | B82Y 15/00 |
| | | | 235/462.01 |
| 2003/0052169 A1 * | 3/2003 | Tsikos | G06K 7/10 |
| | | | 235/454 |
| 2003/0137669 A1 * | 7/2003 | Rollins | G01B 11/2441 |
| | | | 356/479 |
| 2006/0132790 A1 * | 6/2006 | Gutin | G01B 9/02034 |
| | | | 356/479 |
| 2006/0247514 A1 * | 11/2006 | Panasyuk | G01J 3/10 |
| | | | 600/410 |
| 2007/0051601 A1 * | 3/2007 | Wang | H04M 1/0216 |
| | | | 200/284 |
| 2007/0057182 A1 * | 3/2007 | Feuerbaum | H01J 37/3056 |
| | | | 250/310 |
| 2007/0093702 A1 * | 4/2007 | Yu | A61B 5/14552 |
| | | | 600/326 |
| 2008/0097172 A1 * | 4/2008 | Sawada | G01N 21/49 |
| | | | 600/310 |
| 2008/0154126 A1 * | 6/2008 | Culver | A61B 5/0042 |
| | | | 250/363.07 |
| 2009/0177094 A1 * | 7/2009 | Brown | A61B 5/0066 |
| | | | 606/2 |
| 2009/0202251 A1 * | 8/2009 | Shibayama | H01L 31/0203 |
| | | | 398/138 |
| 2009/0284748 A1 * | 11/2009 | Melman | G01B 9/02091 |
| | | | 356/479 |
| 2010/0004741 A1 * | 1/2010 | Gupta | A61F 2/1613 |
| | | | 623/6.22 |
| 2010/0046234 A1 * | 2/2010 | Abu-Ageel | H04N 9/3111 |
| | | | 362/296.01 |
| 2010/0056928 A1 * | 3/2010 | Zuzak | G01J 3/2823 |
| | | | 356/302 |
| 2010/0226646 A1 * | 9/2010 | Chan | G01M 11/083 |
| | | | 398/28 |
| 2011/0054277 A1 | 3/2011 | Pinter et al. | |
| 2011/0082355 A1 | 4/2011 | Eisen et al. | |

(56) References Cited

U.S. PATENT DOCUMENTS

| | | | |
|---|---|---|---|
| 2011/0087108 A1* | 4/2011 | Onoe | A61B 5/0261 600/473 |
| 2011/0196244 A1 | 8/2011 | Ribas Ripoll et al. | |
| 2012/0130215 A1 | 5/2012 | Fine et al. | |
| 2012/0232402 A1* | 9/2012 | MacFarlane | A61B 5/0075 600/473 |
| 2013/0131475 A1 | 5/2013 | Eisen et al. | |
| 2013/0190630 A1 | 7/2013 | Borgos | |
| 2013/0204112 A1 | 8/2013 | White et al. | |
| 2013/0278631 A1* | 10/2013 | Border | G06Q 30/02 345/633 |
| 2014/0094666 A1 | 4/2014 | Fine | |
| 2014/0118695 A1* | 5/2014 | Shimada | A61B 3/1015 351/206 |
| 2014/0120319 A1* | 5/2014 | Joseph | H04N 13/254 348/46 |
| 2014/0313524 A1 | 10/2014 | Banyay et al. | |
| 2014/0316286 A1 | 10/2014 | Addison et al. | |
| 2015/0157224 A1 | 6/2015 | Carmon et al. | |
| 2015/0201854 A1 | 7/2015 | Hong et al. | |
| 2016/0106327 A1 | 4/2016 | Yoon et al. | |
| 2016/0157736 A1 | 6/2016 | Huang et al. | |
| 2016/0183882 A1 | 6/2016 | Henley et al. | |
| 2016/0195473 A1* | 7/2016 | Fujiwara | G01N 21/4795 250/553 |
| 2016/0242647 A1* | 8/2016 | Ishii | A61B 5/165 |
| 2016/0287107 A1 | 10/2016 | Szabados et al. | |
| 2016/0360966 A1* | 12/2016 | Ishii | G16C 10/00 |
| 2017/0007138 A1* | 1/2017 | Kim | A61B 5/14552 |
| 2017/0014037 A1 | 1/2017 | Coppola et al. | |
| 2017/0065184 A1 | 3/2017 | Barak | |
| 2017/0105618 A1* | 4/2017 | Schmoll | G02B 21/0056 |
| 2017/0164878 A1* | 6/2017 | Connor | G09B 19/00 |
| 2017/0188851 A1* | 7/2017 | LeBoeuf | A61B 5/6803 |
| 2017/0231513 A1 | 8/2017 | Presura et al. | |
| 2018/0020962 A1* | 1/2018 | Yu | A61B 5/0059 600/324 |
| 2018/0110423 A1 | 4/2018 | Presura et al. | |
| 2018/0160913 A1 | 6/2018 | Fine | |
| 2018/0202927 A1* | 7/2018 | Isikman | G01N 33/00 |
| 2018/0228363 A1* | 8/2018 | Frisken | A61B 3/0025 |
| 2018/0263519 A1 | 9/2018 | Gu | |
| 2019/0041736 A1* | 2/2019 | Grunnet-Jepsen | G06T 7/521 |
| 2019/0046056 A1 | 2/2019 | Khachaturian et al. | |
| 2019/0053721 A1 | 2/2019 | Boas et al. | |
| 2019/0094564 A1* | 3/2019 | Rivera | G02B 27/48 |
| 2019/0167118 A1 | 6/2019 | Vilenskii et al. | |
| 2019/0175030 A1 | 6/2019 | Verkruijsse et al. | |
| 2019/0343442 A1 | 11/2019 | Aung et al. | |
| 2019/0369650 A1* | 12/2019 | Swanson | G02B 6/04 |
| 2020/0011995 A1* | 1/2020 | Send | G01S 3/783 |
| 2020/0143534 A1* | 5/2020 | Wright | G06T 7/0012 |
| 2020/0158548 A1 | 5/2020 | Rice et al. | |
| 2020/0214602 A1 | 7/2020 | Narumi et al. | |
| 2020/0237272 A1* | 7/2020 | Lin | G02B 21/14 |
| 2020/0249492 A1* | 8/2020 | Maes | G02B 27/0961 |
| 2021/0000385 A1 | 1/2021 | Warren et al. | |
| 2021/0022623 A1 | 1/2021 | Rice et al. | |
| 2021/0161408 A1* | 6/2021 | Wakita | G01P 5/20 |
| 2021/0267471 A1 | 9/2021 | Bonomi et al. | |
| 2021/0321887 A1* | 10/2021 | Fukazawa | A61B 1/045 |
| 2021/0338083 A1* | 11/2021 | Sie | A61B 5/6803 |
| 2021/0386310 A1 | 12/2021 | Hong et al. | |
| 2021/0405518 A1* | 12/2021 | Lablans | H04N 23/69 |
| 2022/0015649 A1 | 1/2022 | Ikuta et al. | |
| 2022/0018762 A1* | 1/2022 | Ekin | A61B 5/1451 |
| 2022/0019861 A1 | 1/2022 | Durr et al. | |
| 2022/0039679 A1 | 2/2022 | Califa et al. | |
| 2022/0061644 A1* | 3/2022 | Fontaine | A61B 5/745 |
| 2022/0104822 A1* | 4/2022 | Shelton, IV | A61B 17/1155 |
| 2022/0196557 A1 | 6/2022 | Zheng et al. | |
| 2022/0265158 A1 | 8/2022 | Tokura | |
| 2023/0048766 A1* | 2/2023 | Frey | G01S 7/4816 |
| 2023/0064006 A1* | 3/2023 | Kim | G03B 30/00 |
| 2023/0148885 A1 | 5/2023 | Bechtel et al. | |
| 2023/0148886 A1 | 5/2023 | Bechtel et al. | |
| 2023/0164444 A1* | 5/2023 | Yang | H04N 23/88 348/335 |
| 2023/0277075 A1 | 9/2023 | Pantelopoulos et al. | |
| 2023/0296510 A1* | 9/2023 | Xu | G01N 21/4788 356/337 |
| 2023/0320598 A1 | 10/2023 | Khine et al. | |
| 2023/0347029 A1 | 11/2023 | Corso et al. | |
| 2023/0397818 A1 | 12/2023 | Newhouse et al. | |
| 2023/0401747 A1 | 12/2023 | Dunn et al. | |
| 2024/0032790 A1* | 2/2024 | Patel | A61B 3/10 |
| 2024/0041342 A1 | 2/2024 | Lai et al. | |
| 2024/0074667 A1 | 3/2024 | Rick et al. | |
| 2024/0108289 A1 | 4/2024 | Bechtel et al. | |
| 2024/0115212 A1 | 4/2024 | Jang | |
| 2024/0156355 A1 | 5/2024 | O'Brien et al. | |

FOREIGN PATENT DOCUMENTS

| | | |
|---|---|---|
| CN | 211131004 U | 7/2020 |
| CN | 112639582 A | 4/2021 |
| CN | 114466549 A | 5/2022 |
| WO | WO 2020/114989 A1 | 6/2020 |
| WO | WO 2023/245149 A2 | 12/2023 |
| WO | WO 2024/052289 A1 | 3/2024 |

OTHER PUBLICATIONS

Goodman, J. W., "Some fundamental properties of speckle", Journal of the Optical Society of America, Nov. 1976, pp. 1145-1150, vol. 66, No. 11, Optical Society of America.

Robinson, M. B. et al., "Interferometric diffuse correlation spectroscopy improves measurements at long source-detector separation and low photon count rate", Journal of Biomedical Optics, Sep. 30, 2020, pp. 097004-1 through 097004-12, vol. 25(9), SPIE.

Sdobnov, A. Y. et al. "Speckle dynamics under ergodicity breaking", Journal of Physics D: Applied Physics, Mar. 26, 2018, pp. 1-21, vol. 51, No. 15, IOP Publishing Ltd.

Website: "FlowMet Peripheral Blood Flow Monitoring System", updated Oct. 2022, printed Dec. 7, 2022, 7 pages, https://www.medtronic.com/us-en/healthcare-professionals/products/cardiovascular/intraprocedural-monitoring/flowmet.html.

Website: "0.07mm Dia., TO-46 Package, InGaAs Photodiode", 2022, printed Dec. 7, 2022, 1 page, Edmund Optics Inc., https://www.edmundoptics.com/p/ingaas-detector-70mum-dia-to-46/12571/.

Xu, J. et al., "Interferometric speckle visibility spectroscopy (ISVS) for human cerebral blood flow monitoring", APL Photonics, Dec. 4, 2020, pp. 126102-1 through 126102-10, vol. 5. AIP Publishing.

U.S. Appl. No. 17/703,920, filed Mar. 24, 2022.

International Search Report and Written Opinion of the International Searching Authority, mailed Jan. 2, 2023, corresponding to PCT/EP2022/074876, 13 pages.

Zalevsky, Z. et al., "Novel Approaches for Near and Far Field Super Resolved Imaging", 22nd Congress of the International Commision for Optics: Light for the Development of the World, Proc. of SPIE, Sep. 15, 2011, pp. 80116M-1 through 80116M-11, vol. 8011, No. 1, SPIE.

U.S. Office Action for U.S. Appl. No. 17/703,920, dated Apr. 5, 2024, 11 pages.

U.S. Notice of Allowance for U.S. Appl. No. 17/703,920, dated Jul. 31, 2024, 10 pages.

\* cited by examiner

Aperture Array
EN FACE VIEW

OPTICAL SPECKLE RECEIVER

RELATED APPLICATIONS

The present application is a continuation of U.S. patent application Ser. No. 17/703,920, filed Mar. 24, 2022, entitled "OPTICAL SPECKLE RECEIVER", which claims priority to and the benefit of U.S. Provisional Application No. 63/243,021, filed Sep. 10, 2021, entitled "OPTICAL RECEIVER"; the entire contents of all of the documents identified in this paragraph are incorporated herein by reference.

FIELD OF THE INVENTION

The present invention relates to an optical speckle receiver, comprising an optical detector and an aperture array or a lens array, an optical transceiver, and a wearable device.

BACKGROUND

In various clinical or home health care settings, obtaining optical data (for example spectrophotometric data) from tissue of a subject may be advantageous, e.g., to sense levels of chemical compounds (for example glucose) in the tissue, to measure other characteristics (for example temperature) of the tissue, or to distinguish different kinds of tissue (for example healthy from diseased tissue).

In some cases, the spectrophotometric data includes speckle data as obtained by a speckleplethysmography device. Speckle fluctuations due to the interaction of coherent light with dynamic scatterers (for example red blood cells) can be quantified to monitor various physiological parameters (for example blood flow). Speckle size-to-sensor pixel size matching is typically achieved via single mode fiber for photodiodes or an aperture or multimode fiber with or without a lens system for image sensors.

However, such systems are unsuited for integration into wearable devices as either the amount of light collected is too low for optimal use or the distance between the tissue and the optical detector is too large. Wearable spectrophotometric devices broaden the applications of spectrophotometry and improve compliance in monitoring. There is a desire then to facilitate the integration of optical receivers suitable for receiving speckle signals with miniaturized, wearable devices.

SUMMARY

Accordingly, in some embodiments, the present invention provides an optical speckle receiver, which may be referred to as an optical receiver, for receiving a speckle signal from a sample or surface, the optical speckle receiver comprising an optical detector and an aperture array and/or a lens array, wherein, the aperture array and/or lens array respectively comprise a plurality of apertures or lenses and is located between, or in-between, the surface or sample and the optical detector such that the received speckle pattern is obtained from multiple discrete sample locations.

Receiving a speckle pattern from multiple sample locations may be counterintuitive as adding M uncorrelated speckle patterns on an intensity basis reduces speckle contrast by 1/sqrt(M), which is undesirable. However, if the speckle patterns are generated by the same coherent source and are physically separated by a distance larger than the correlation distance such that the patterns generated are independent, then the speckle patterns add on a complex amplitude basis, not intensity, and the speckle contrast is not reduced. [J. W. Goodman, "Some fundamental properties of speckle" J. Opt. Soc. Am. 66(11):1145-1150, 1976].

By providing such an aperture array or lens array, sampling of a speckle pattern can be undertaken by a compact sensor with a reduced height from the sample or surface whilst maintaining an acceptable signal-to-noise ratio. Further, the aperture array or lens array can ensure that only light which has more deeply interacted with the sample, and not just the surface, is detected.

Optional features of the invention will now be set out. These are applicable singly or in any combination with any aspect of the invention.

In some, but not all, examples, the plurality of apertures or lenses includes an element of ordering or structure but in yet other examples the apertures or lenses in the respective arrays may be unordered or unstructured. By aperture, it may be meant an inlet or opening for light in the otherwise opaque plate. By lens, it may be meant an optical element with focal length designed to produce optimal speckle size as compared to sensor pixel size based on the distance between the optical element(s) and the sensor.

The aperture array or lens array being located between, or in-between, the surface of the sample and the optical detector may be such that the speckle pattern at the surface can be viewed by the optical detector through each of the apertures.

The sample or surface may be tissue. By tissue, it is meant biological tissue such as human skin. In some examples, the surface may be the skin of a patient who is to have a biomarker value derived from the speckle signal. The skin may be skin on or around the wrist, specifically a dorsal portion of the wrist or ulnar or radial portion of the wrist.

The aperture array may be a plate, and the plate may define or include within it a plurality of holes, each hole corresponding to an aperture of the aperture array. The holes may have a uniform cross-section as they extend through the plate, or may have a cross-section which varies as a function of depth.

The aperture array may include an array of single mode or multi-mode fibers, each single mode or multi-mode fiber corresponding to an aperture of the aperture array. That is, each aperture in the aperture array may be provided with an end of an optical fiber. The aperture array may be a plate in which each of the optical fibers are integrally formed.

The optical detector may be a photodiode or a pixel array such as an image sensor. The optical detector may include a plurality of photodiodes or may, in some examples, be a charge-coupled device.

The relationship between aperture diameter (D) of apertures in the aperture array and the distance (Z) between the tissue or surface and the optical detector is governed by $S = \lambda Z/D$ where S is the speckle diameter and $\lambda$ is the wavelength of light; and wherein the parameters are chosen such that Z has a value of less than 5 cm, less than 2 cm, less than 1 cm, less than 0.5 cm, or less than 0.1 cm. By wavelength of light, it may be meant the wavelength of the light which is forming the speckle. All of the apertures in the aperture array may have a same cross-sectional shape, for example a circle, square, rectangle, or triangle. In other examples, some of the apertures in the aperture array may have different cross-sections to other apertures in the aperture array. The apertures in the aperture array may be identically dimensioned (e.g. having a same diameter where circular), or some apertures in the aperture array may have dimensions which are different to other apertures in the aperture array.

The relationship between lens $f_{\#}$, magnification (M) and the distance (Z) between the tissue or surface and the optical detector is governed by $S \approx 1.2(1+M)\lambda f_{\#}$ where $f_{\#}$ is the ratio between the lens focal distance and the effective aperture of the lens. The parameters may be chosen such that Z has a value of less than 5 cm, less than 2 cm, less than 1 cm, less than 0.5 cm, or less than 0.1 cm. By wavelength of light, it may be meant the wavelength of the light which forms the speckle. The lenses in the lens array may be spherical, aspherical, cylindrical, or may be customized to any particular shape that serves the purpose of projecting light onto the detector with desired speckle size.

In a second aspect, embodiments of the invention provide an optical transceiver comprising the optical speckle receiver of the first aspect and a coherent light source. The optical transceiver may have any one, or any combination insofar as they are compatible, of the optional features as set out with reference to the first aspect.

The coherent light source may operate at one or more ultraviolet to far infrared (IR) wavelengths. Herein, the wavelength range may be understood as being between 280 nm and 1 mm. In some examples the coherent light source may operate at 1300 nm. The coherent light source may be a laser.

The coherent light source may include a coherent light source operating at one or more visible wavelengths.

The optical transmitter and optical speckle receiver together make an optical transceiver which may be arranged in a reflection mode such that light from the coherent light source interacts with the tissue and produces speckle at the tissue which is captured by the detector. The aperture array and/or lens array, placed between the tissue and detector, receives speckle from the tissue (both the surface and tissue beneath the surface) and passes this light through its apertures or lenses to the optical detector. The aperture array and/or lens array also helps manipulate the size of the speckles received by the detector. The relationship between the aperture array or lens array, the tissue, and the light source can be designed to prevent specular reflectance (that is, to ensure that light interacts with dynamic scatterers in the tissue).

The transceiver may be arranged in a transmission mode, such that light from the coherent light source produces speckle through the tissue, the aperture positioned to receive light transmitted through the tissue, through its apertures or lenses, to the optical detector.

In a third aspect, embodiments of the invention provide a wearable device including the optical receiver of the first aspect or the optical transceiver of the second aspect. The optical receiver may have any one, or insofar as they are compatible, any combination of the optional features as set out with reference to the first aspect. The optical transceiver may have any one, or insofar as they are compatible, any combination of the optional features as set out with reference to the second aspect.

The aperture plate and/or lens array may form a portion of an outer casing of the wearable device.

The lens array and aperture array may operate independently or together in the same device.

In a fourth aspect, embodiments of the invention provide an aperture array or lens array respectively comprising a plurality of apertures or lenses, the aperture array or lens array configured to be located in-between tissue and a photodiode or optical detector such that speckle patterns at the tissue can be acquired by the optical detector through the plurality of apertures or lenses (that is, combined on the photodiode or optical detector).

The invention includes the combination of the aspects and preferred features described except where such a combination is clearly impermissible or expressly avoided.

BRIEF DESCRIPTION OF THE DRAWINGS

Embodiments of the invention will now be described by way of example with reference to the accompanying drawings in which.

DETAILED DESCRIPTION AND FURTHER OPTIONAL FEATURES

Figure 1A:
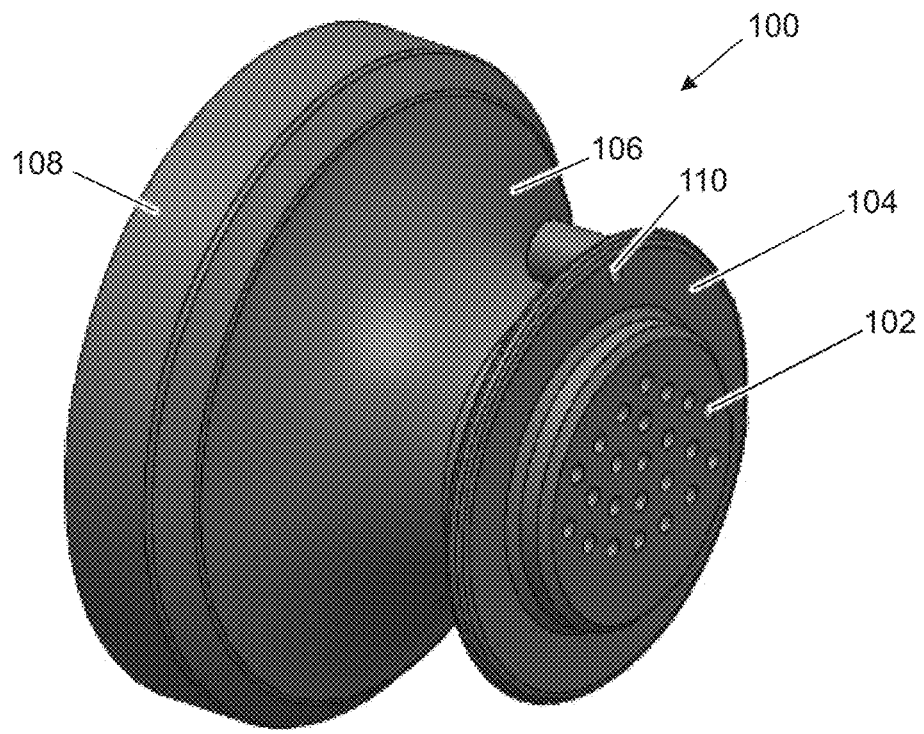
FIGS. 1A and 1B show an aperture array from a perspective and front-on view respectively.
Figure 1B:
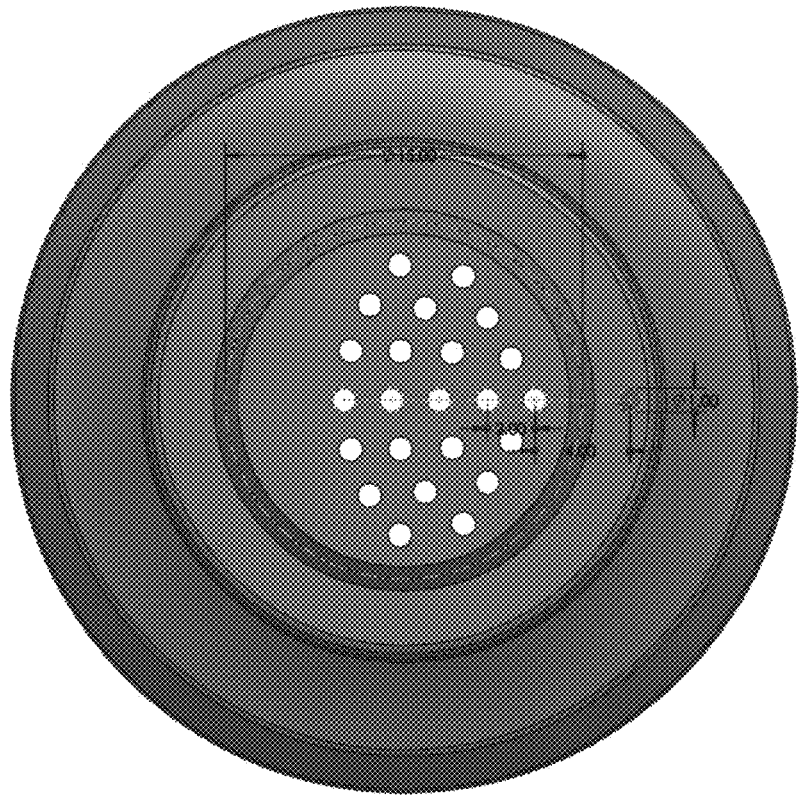

Aspects and embodiments of the present invention will now be discussed with reference to the accompanying figures. Further aspects and embodiments will be apparent to those skilled in the art. All documents mentioned in this text are incorporated herein by reference FIGS. 1A and 1B show an aperture array 100 from a perspective and front-on view respectively. The aperture array in this example includes a plurality of apertures 102. In this example the apertures are located on a flange or protrusion 104 spaced from a base 106 via a neck 108. As can be seen in FIG. 1B, the apertures have an outer diameter of 1 mm. The flange or protrusion has a diameter of around 15 mm. The apertures are arranged in an array, in this example being formed of 23 apertures. Apertures within a row are spaced by 2 mm (centre to centre). An input aperture 110 is provided, offset both vertically and horizontally from the aperture array, and through which a sample is illuminated.

Figure 2A:
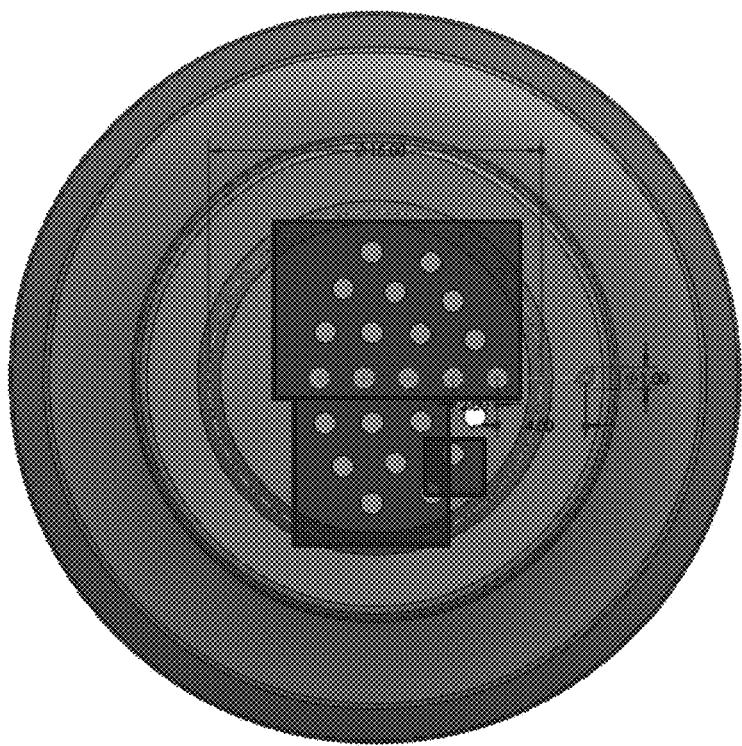
FIGS. 2A, 2B, and 2C show the aperture array in various configurations as used during testing.
Figure 2B:
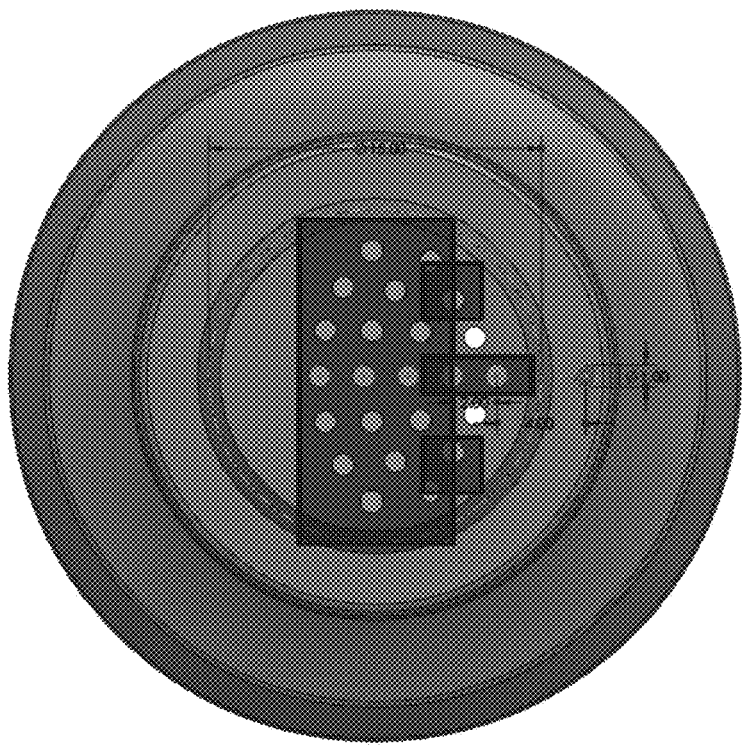
Figure 2C:
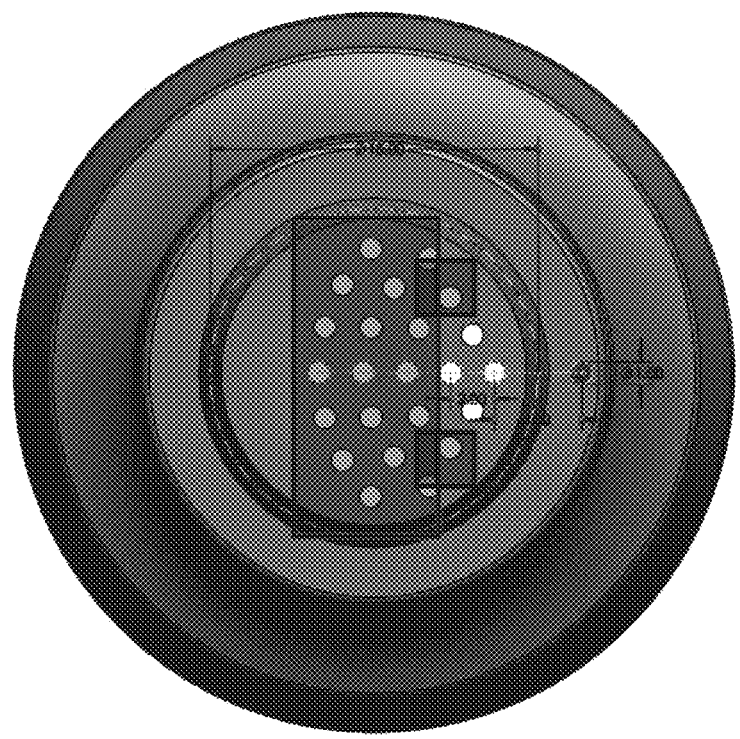

FIGS. 2A, 2B, and 2C show the aperture array in various configurations as used during testing. In the first configuration, shown in FIG. 2A and referred to as the 'one aperture' configuration, all apertures bar one are blocked off so that light can only pass through the single aperture. In the second configuration, show in FIG. 2B and referred to as the 'two aperture' configuration, all apertures bar two are blocked off. In this example, the two unblocked apertures are symmetrically disposed in the array with respect to a line passing horizontally through the aperture array. In the third configuration, show in FIG. 2B and referred to as the 'four aperture' configuration, all apertures bar four are blocked off. In this example, the four unblocked apertures are symmetrically disposed in the array with respect to a line passing horizontally through the aperture array.

Figure 3:
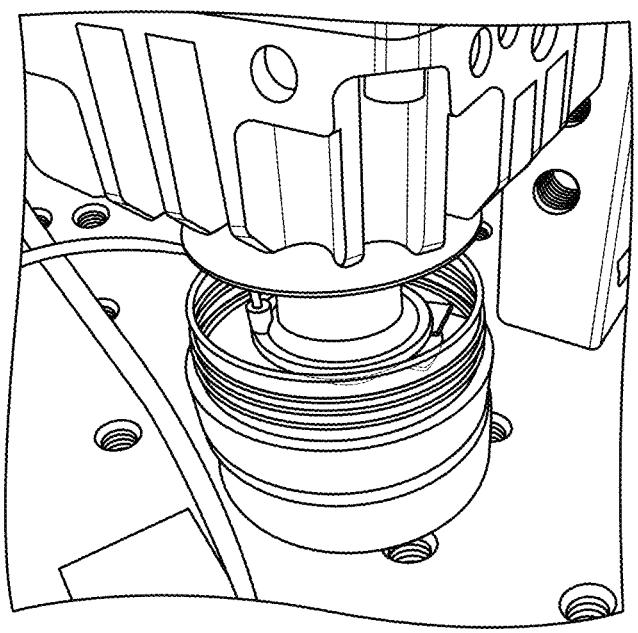
FIG. 3 shows an experimental setup used for testing the aperture array.

FIG. 3 shows an experimental setup used for testing the aperture array in each of the three configurations. A Keysight power supply was used to drive a Q-Photonics DFB laser with an operating wavelength 1300 nm and operating power of 10 mW. Data was acquired through a National Instruments DAQ. The optical receiver was an WiDy SEnS 640V-STEP gated mode camera, and the aperture array was connected to it such that light from the laser passed through a gelatine phantom and back through the aperture array to the camera. The camera's pixels had an active area of around 15 µm, and the apertures in the aperture array had a diameter of 1 mm. The camera sensor was positioned 2.5 cm from the gelatine phantom, and as discussed the operating wavelength of the laser was 1300 nm. The size of the speckles can therefore be calculated as:

$$((1300 \times 10^{-9} \text{ m}) \cdot (2.5 \times 10^{-2} \text{ m}))/(1 \times 10^{-3} \text{ m}) = 32.5 \text{ µm}$$

The speckles therefore had a size which was approximately twice the active area of the pixels. A 7×7 sliding window was used to calculate speckle contrast (using the MATLAB function colfilt). The contrast, K, was calculated as $$K = \frac{\text{std of window}}{\text{mean of window}}.$$

The average speckle contrast was determined from the whole frame, and the average intensity was calculated by averaging the pixel intensities from the whole frame.

During the experiments, the camera mode was set to linear with gain set as high. For the one aperture configuration a 20 ms exposure time was used. For the two aperture configuration a 10 ms exposure time was used. For the four aperture configuration a 5 ms exposure time was used. The data was acquired as a 16-bit TIFF image via Snapshot.

Figure 4:
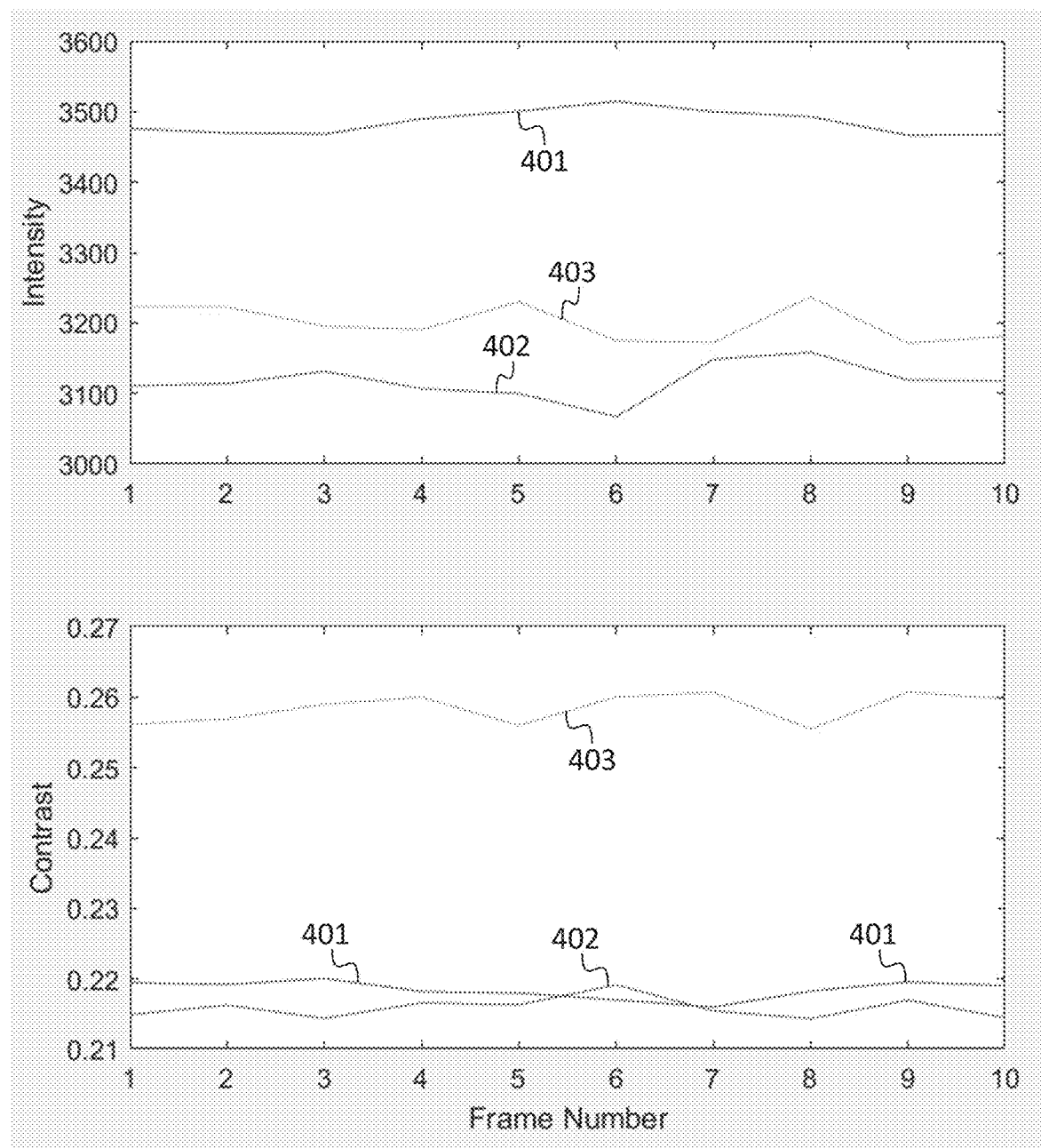
FIG. 4 shows plots of intensity (upper) and contrast (lower) against frame number for the one, two, and four aperture configurations.
Figure 5A:
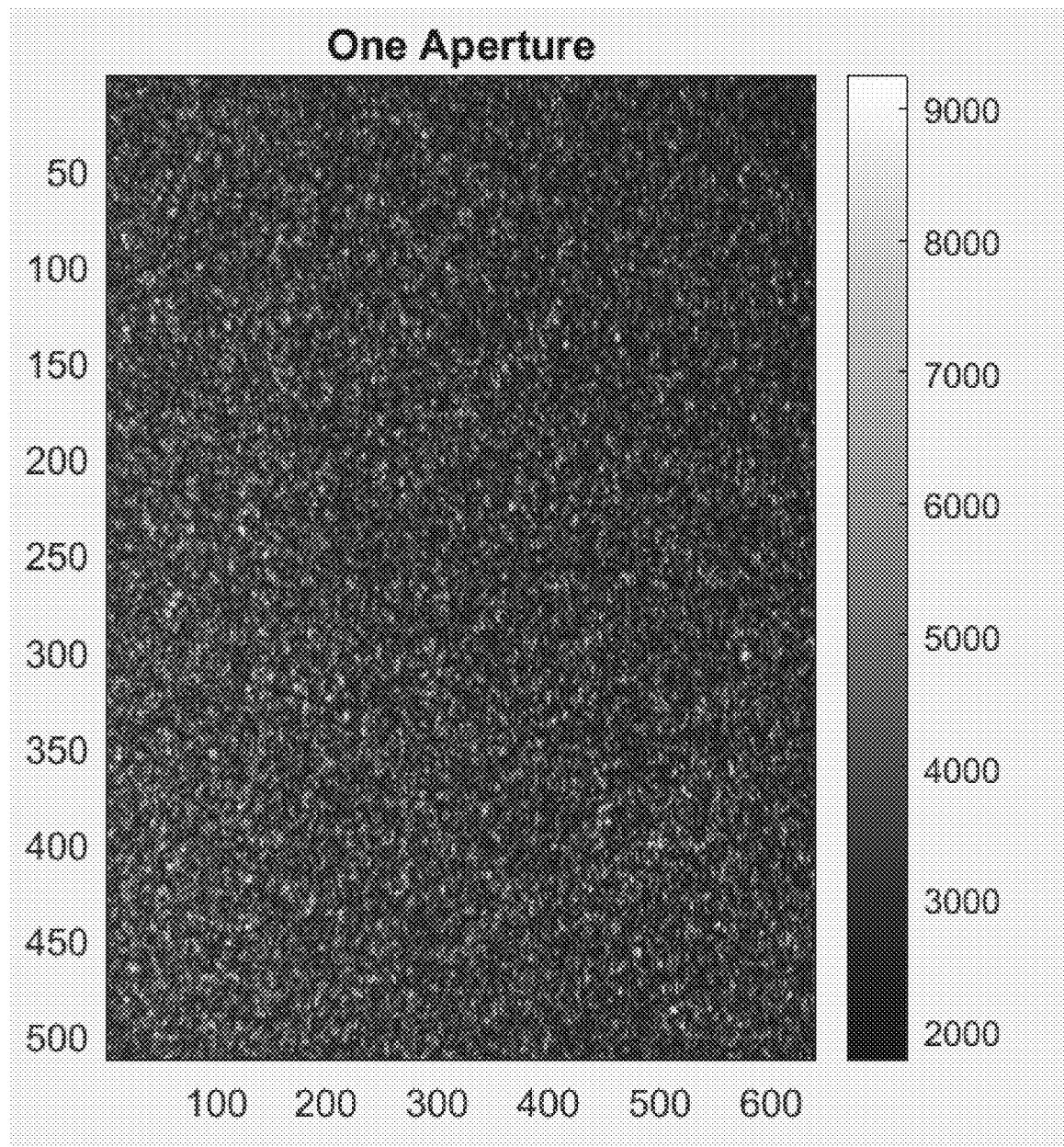
FIGS. 5A, 5B, and 5C show respective sample frames for each of the one, two, and four aperture configurations.
Figure 5B:
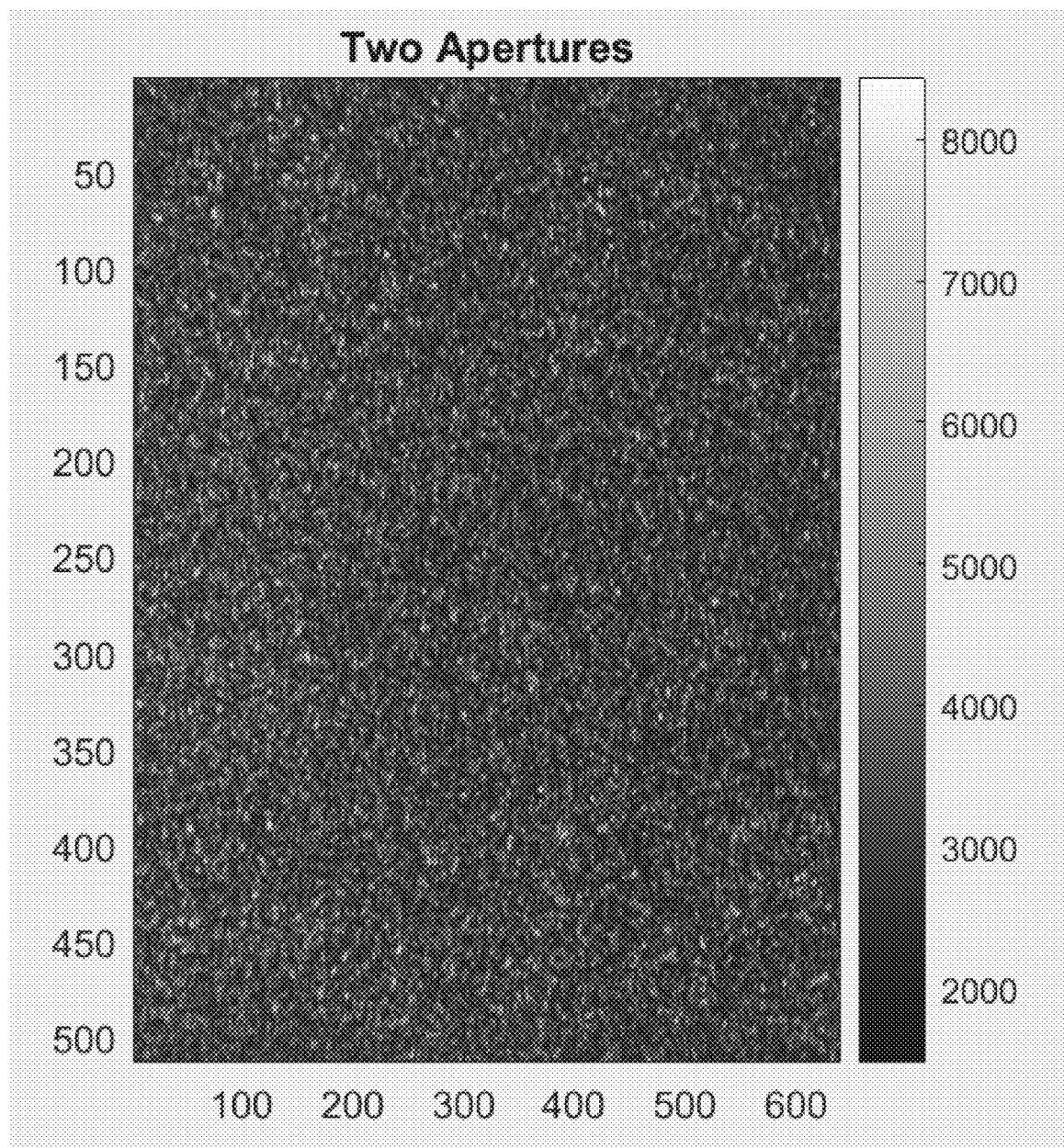
Figure 5C:
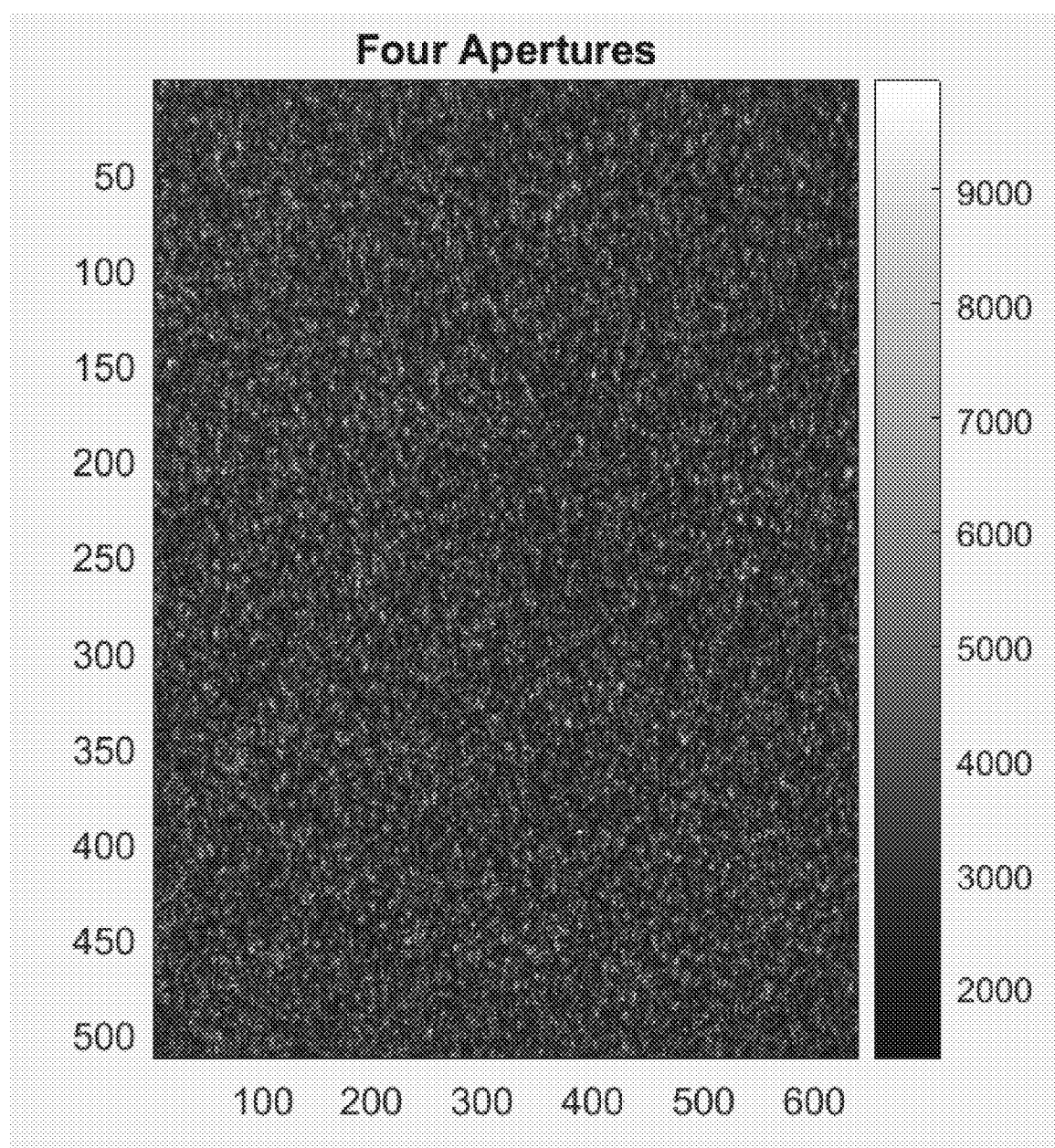

FIG. 4 shows plots of intensity (upper) and contrast (lower) against frame number for the one, two, and four aperture configurations (shown in a first curve 401, a second curve 402, and a third curve 403, respectively, in each of the two plots) as processed through the experimental setup discussed above. Of note is that the average intensity is similar for the different configurations with different exposure times, and increasing the number of apertures does not result in a reduction of contrast. Therefore, it can be understood that the aperture provides more light to the optical receiver and can also reduce the distance needed from the sample (e.g. skin) to the detector. FIGS. 5A, 5B, and 5C show respective sample frames for each of the one, two, and four aperture configurations.

A second experiment was then performed, using the same setup as discussed above but where the gelatine phantom had been replaced with a human finger. 200 images were acquired at 50 frames per second. To derive a spatial speckle contrast, a 7×7 sliding window was applied and then averaged for each image across all of the images. To derive a temporal speckle contrast, the standard deviation was divided by the mean of each pixel over the 200 images and then averaged. Table 1 below shows the results of this:

TABLE 1

| Sample | Apertures | Mean Intensity | Spatial SC ($K_S$) | Temporal SC ($K_t$) | CSD |
|---|---|---|---|---|---|
| Gelatine | 1 | 3201 | 0.2569 | 0.0732 | 0.4433 |
| Gelatine | 4 | 3230 | 0.2429 | 0.0561 | 0.3755 |
| Finger | 1 | 2002 | 0.1421 | 0.1477 | 1.0194 |
| Finger | 4 | 3167 | 0.1916 | 0.2004 | 1.0225 |

CSD is the coefficient of Speckle Dynamics, and is calculated using me equation $$CSD = \frac{2K_t}{K_S + K_t}.$$

The results in Table 1 suggest that the benefit of multiple apertures extend not only to enhancing the spatial speckle contrast, but also the temporal speckle contrast.

Figure 6A:
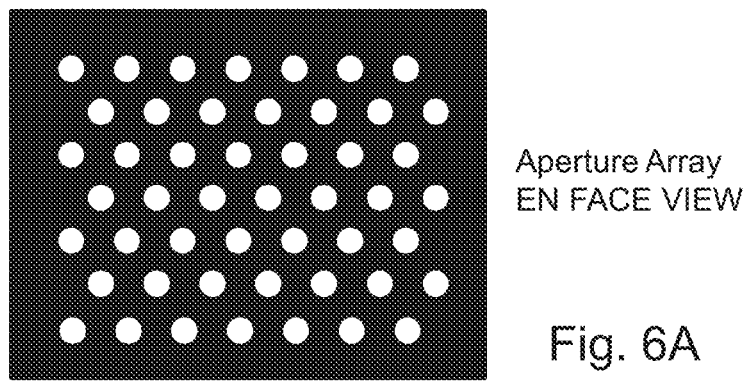
FIG. 6A shows a schematic setup of an aperture array, provided on a plate.
Figure 6B:
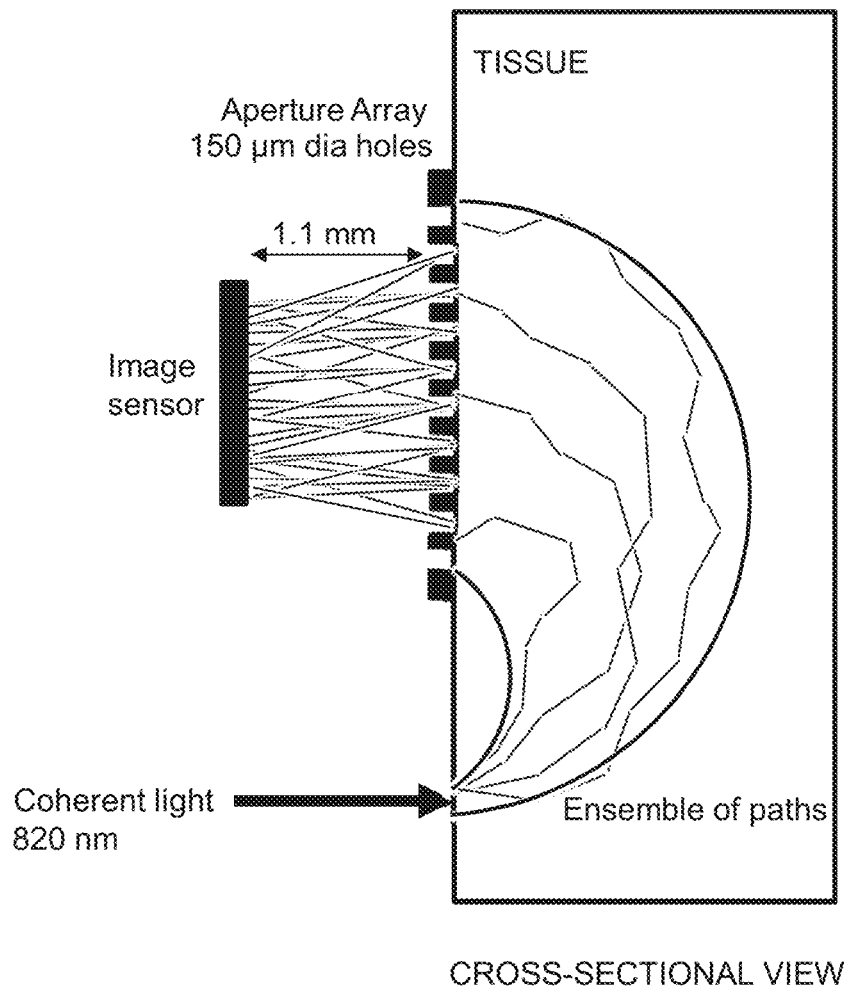
FIG. 6B shows how light passes through the system.

FIG. 6A shows a schematic setup of an optical transceiver using an optical speckle receiver with aperture array and FIG. 6B shows how light passes through the system. Coherent light with a wavelength of around 820 nm illuminates the tissue. The light traverses an ensemble of paths, creating speckle at the output of the tissue surface. An aperture plate comprised of 150 micron diameter holes collects light from different regions of the tissue. The aperture array here is provided as a plurality of holes (which are voids (e.g. unfilled), or holes filled with a light-transmitting material) in a material, but could also be provided as an array of fibres (e.g. an array of fibre optic cables). The light from the aperture array mixes, creating a new speckle pattern on the image sensor, but with the same contrast as would arise from a single aperture. With this aperture size, the image sensor may be placed in close proximity to tissue, for example only 1.1 mm from the aperture plate. For such a system, the speckle size can be calculated using the equation S=λZ/D, and using the values: λ=820 nm; D=150 µm; and Z=1.1 mm a speckle size of 6 µm can be obtained, which is sufficiently large for a sensor with 3 micron pixels.

Figure 7A:
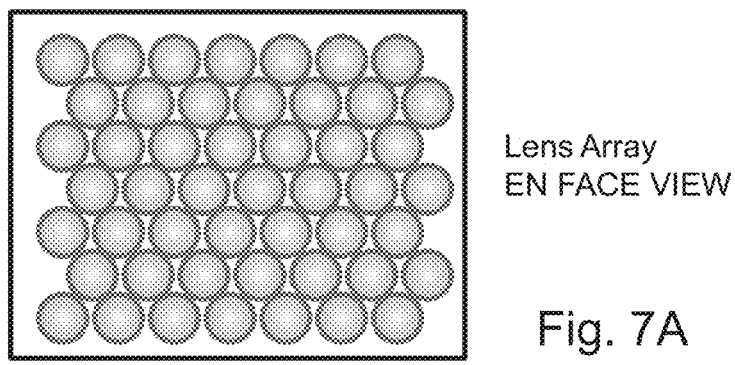
FIG. 7A shows a schematic setup of a lens array and FIG. 7B shows how light passes through the system.
Figure 7B:
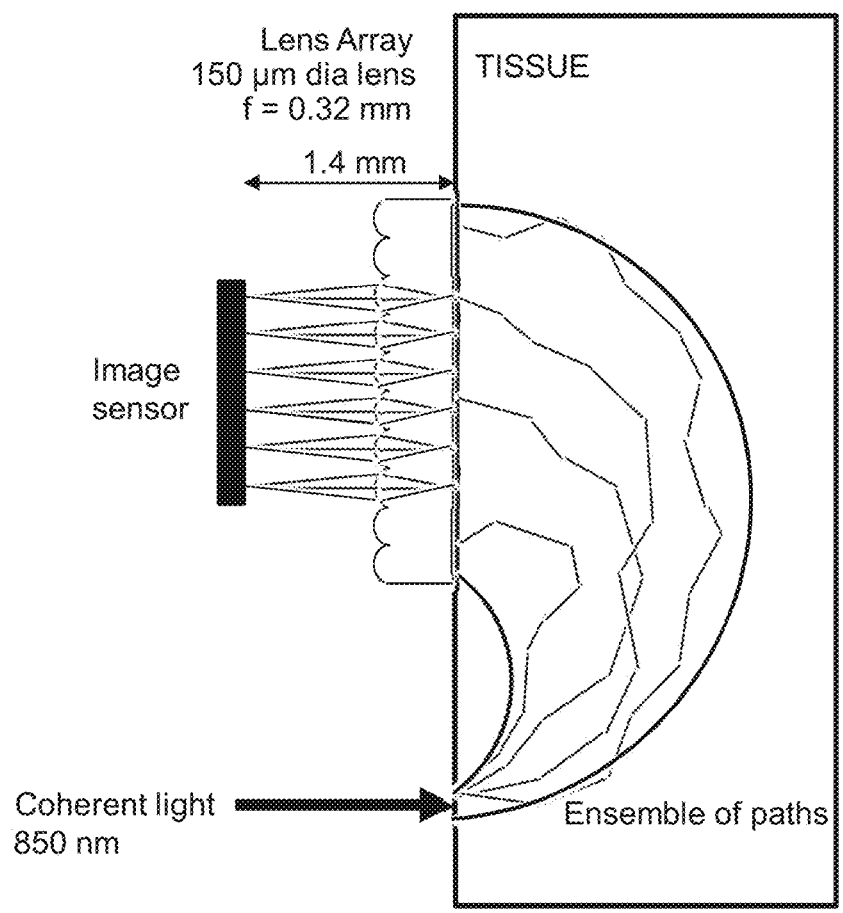

FIG. 7A shows a schematic setup of an optical transceiver using an optical speckle receiver with lens array and FIG. 7B shows how light passes through the system. In this example, a microlens array collects light from different regions of the tissue. The microlens array may be comprised of individual lenses (i.e. physically discrete) or be a monolithic block. The material surrounding the lenses may be clear or opaque to reduce background light. Each microlens has a diameter of 150 microns and a focal length of 0.32 mm. The substrate thickness is such that the distance to the tissue surface is effectively 0.5 mm. From the lens equation, the image is formed at 0.9 mm with magnification of 1.8. For such a system, the speckle size can be calculated using the equation S≈1.2(1+M)λf$_\#$ where f$_\#$ is the ratio between the lens focal distance and the effective aperture of the lens, and using the values: λ=850 nm; f$_\#$=0.3 mm/150 µm; M=1.8. The calculated speckle size is 6.1 microns, which is sufficiently large for a sensor with 3 micron pixels.

Figure 8:
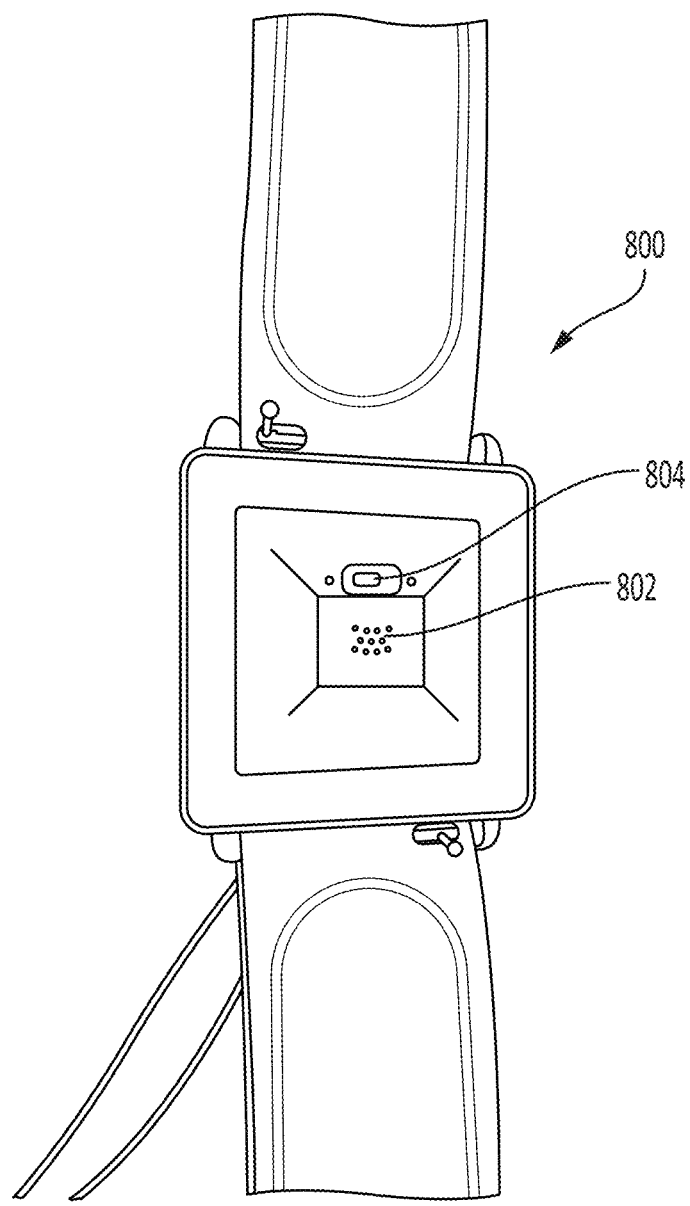
FIG. 8 shows a wearable device including an aperture array.

FIG. 8 shows a wearable device 800 including an aperture array 802. The aperture array is mounted on the rear of the wearable device, which in this example is a wristband including the main device housing and a wrist strap. In use, the aperture array will be pressed against the skin of the user with a gap between the coherent light source 804 and the skin of the user. That is, the aperture array 802 projects further from the wearable, in a direction towards the skin of the user, than the coherent light source 804.

Figure 9:
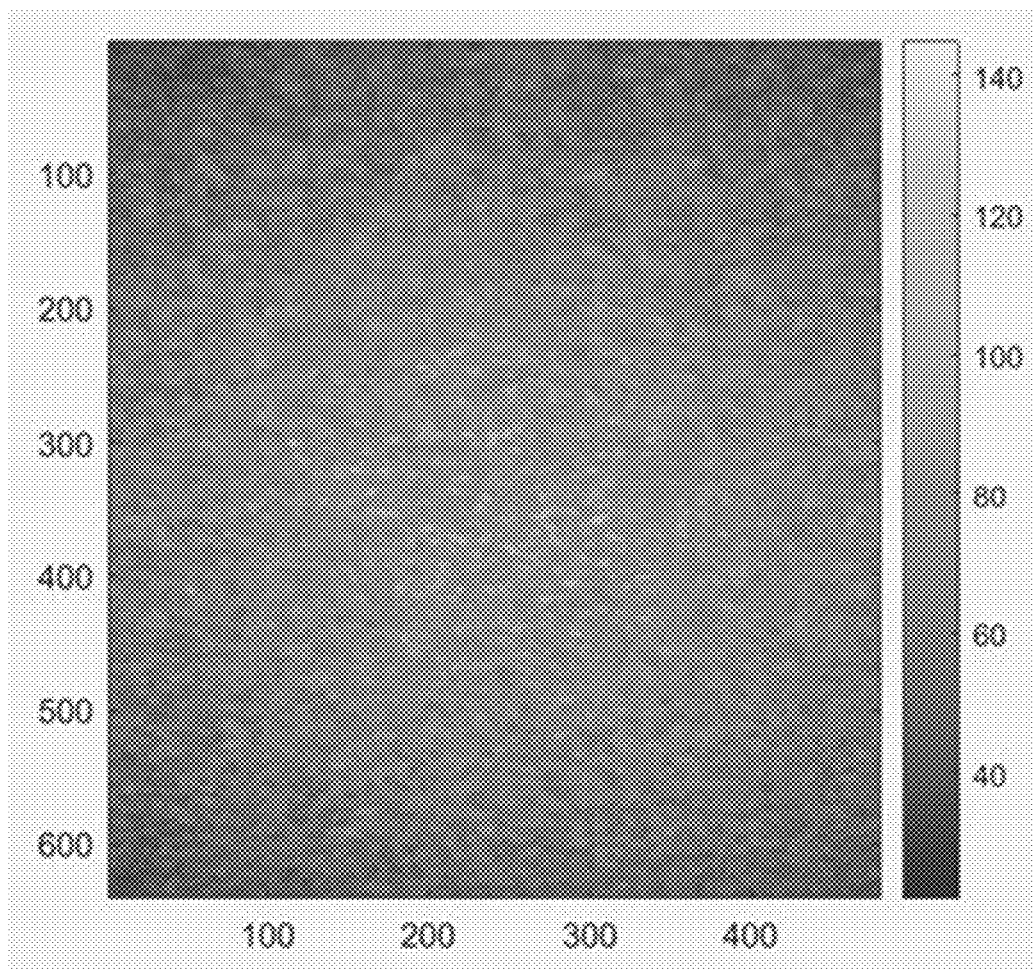
FIG. 9 shows a raw speckle image as acquired by the optical receiver through the aperture array.
Figure 10:
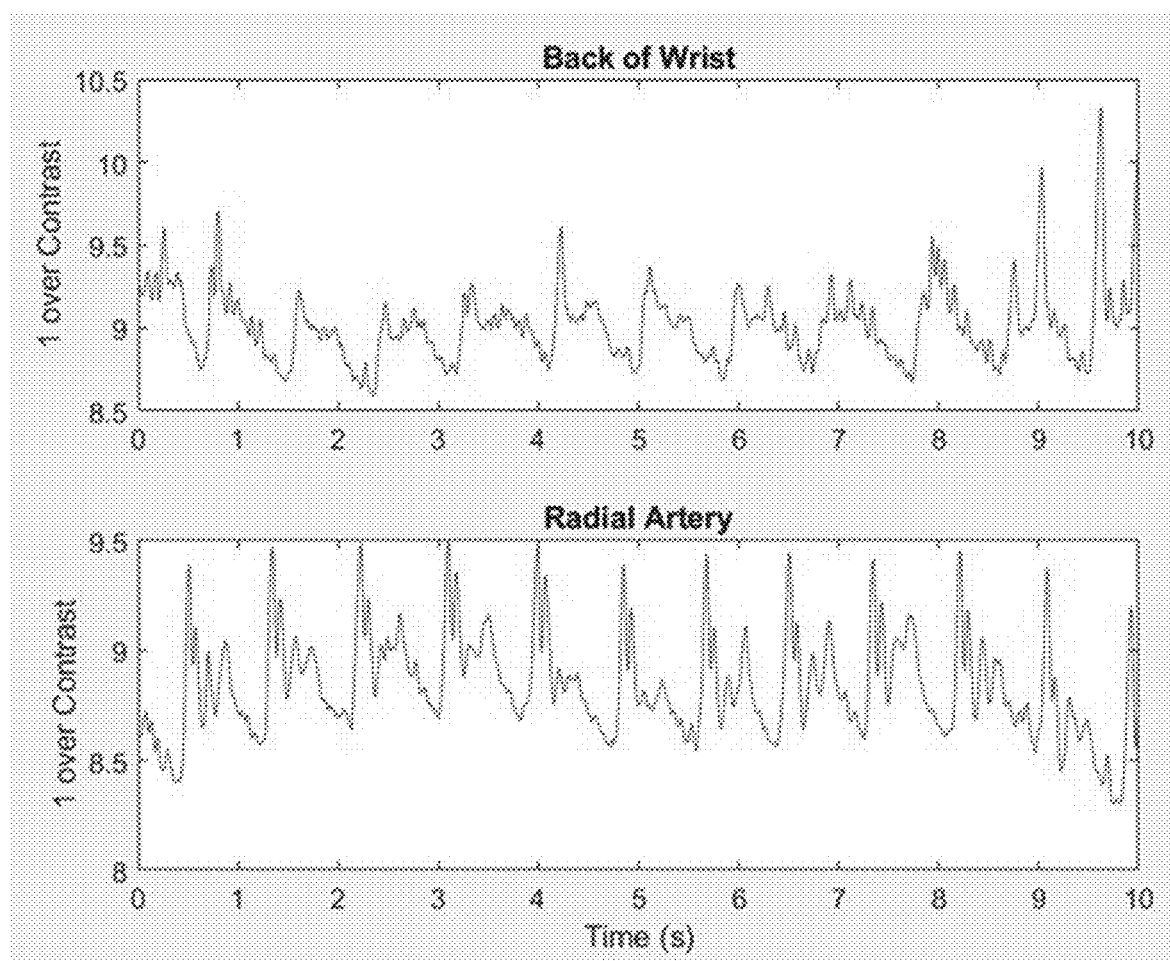
FIG. 10 shows plots of 1 over contrast against time where the optical receiver is located on the back of a person's wrist (upper) and over their radial artery (lower)

FIG. 9 shows a raw speckle image as acquired by the optical receiver through the aperture array. FIG. 10 shows plots of 1 over contrast against time where the optical receiver is located on the back of a person's wrist (upper) and over their radial artery (lower). The data for the plots was arrived at after processing the raw speckle image. As can be seen, pulsating components are visible which indicates the speckle image is suitable to derive the heart rate of the user.

Figure 11A:
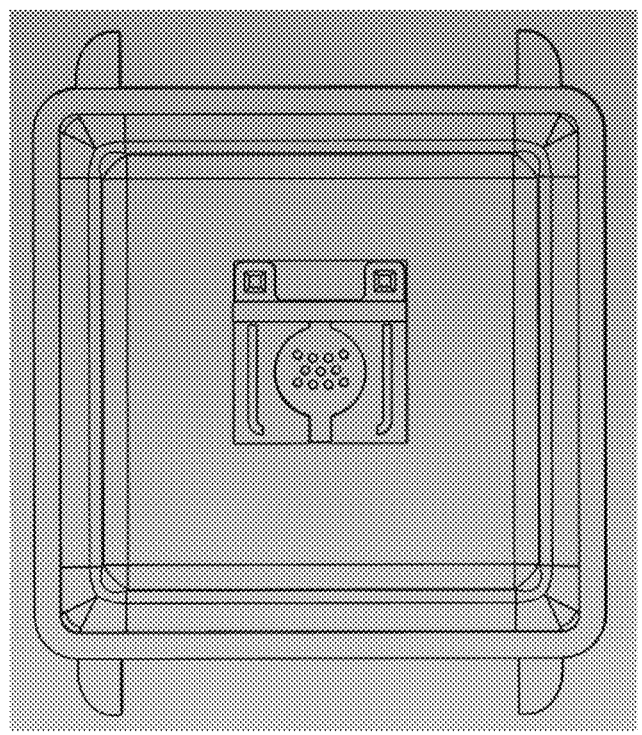
FIG. 11A-11C show CAD images for a wearable from a sensor top side, sensor bottom side, and sensor top side (angle) respectively.
Figure 11B:
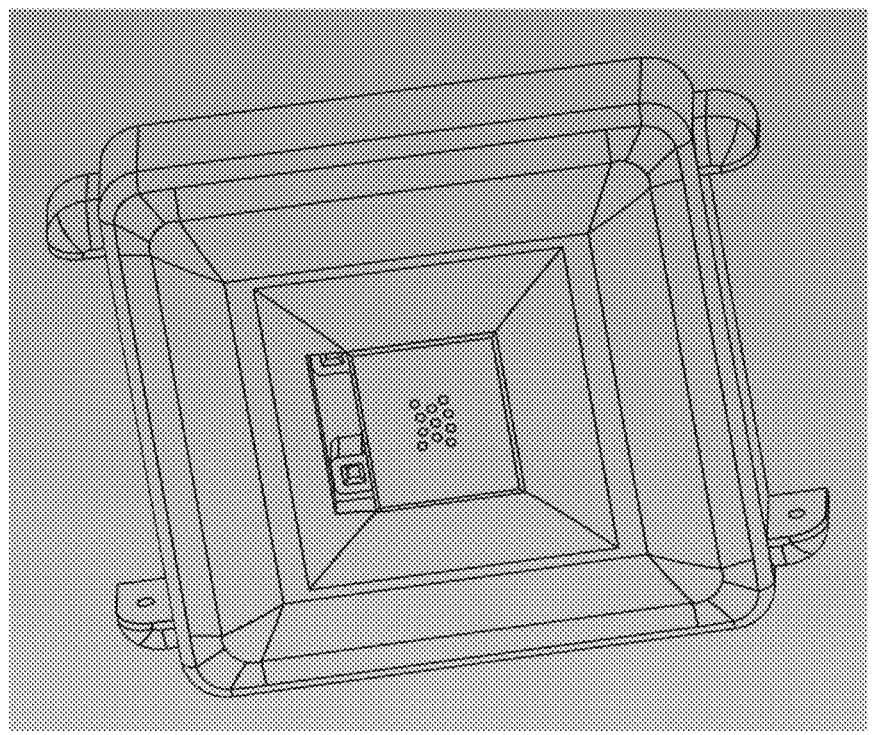
Figure 11C:
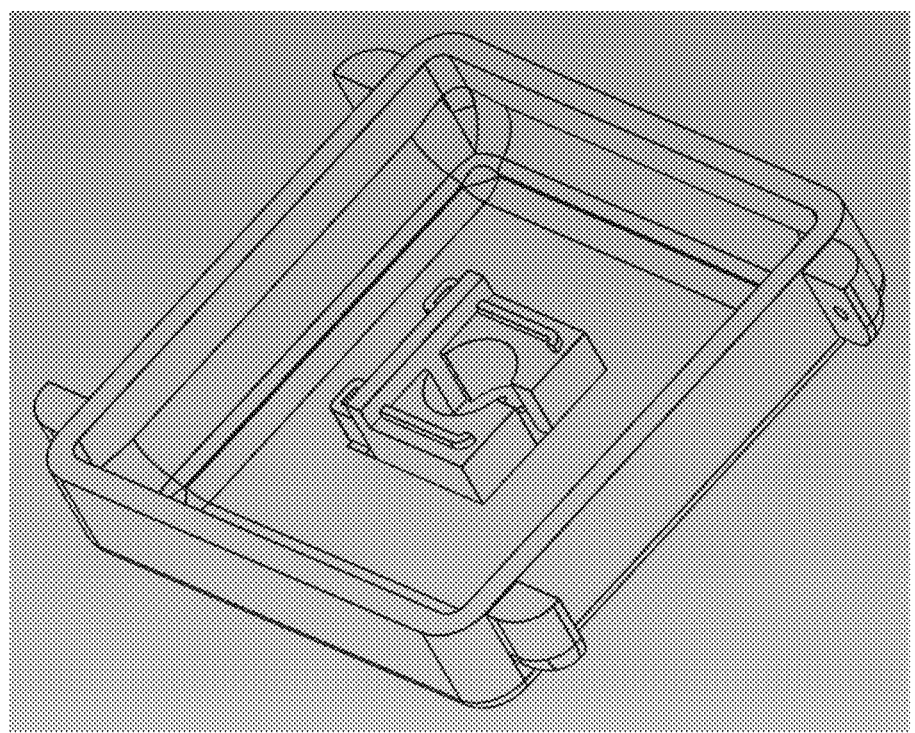

FIG. 11A-11C show CAD images for a wearable from a sensor top side, sensor bottom side, and sensor top side (angle) respectively. The light source and/or apertures for the sensor may be designed to protrude so that they make better contact with the skin. Improved contact may enhance the speckle measurements by reducing specular reflectance.

Figure 12:
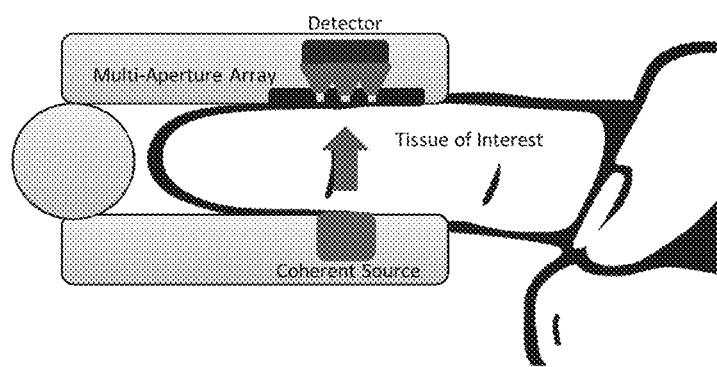
FIG. 12 shows an alternative arrangement for a wearable including an optical receiver and aperture array.
Figure 13:
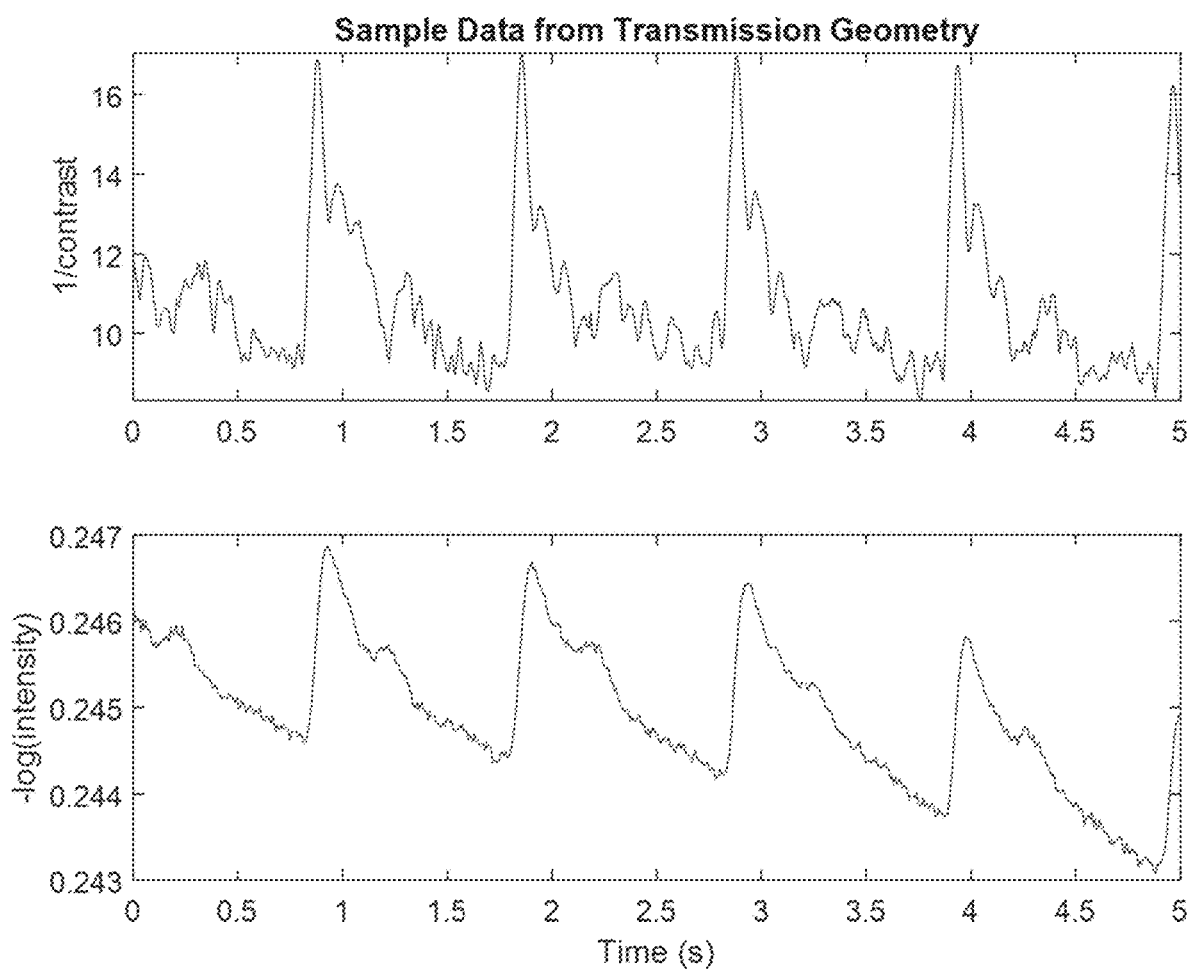
FIG. 13 shows a plot of 1/contrast (upper) and −log (intensity) (lower) against time for data collected from the arrangement in FIG. 12.

FIG. 12 shows an alternative arrangement for a wearable including an optical receiver and aperture array. This arrangement is referred to as a transmission arrangement or transmission mode (as opposed to the arrangement shown in FIGS. 6A and 6B which are reflection arrangements or reflection modes). For example, the wearable may be a ring or similar such that it at least partially encloses a portion of the user. In the transmission mode, the coherent light source is located across a testing region from the aperture array and detector. Tissue of interest, for example a patient's finger, is positioned in the testing region and so the coherent light passes through it to the multi-aperture array and on to the detector. In this example, the transmission arrangement is provided as a finger-clip type device where two generally planar elements are hingedly connected at one end to allow them to move towards and away from each other. The patient introduces their finger between the planar elements and spectrophotonic sampling is performed. FIG. 13 shows a plot of 1/contrast (upper) and −log(intensity) (lower) against time for data collected from the arrangement in FIG. 12. Again, as can be seen, pulsating components are visible which indicates the speckle image is suitable to derive the heart rate of the user.

Depending on the distance from the skin to the detector for speckle matching, increasing the number of holes or apertures in the aperture array may provide increased power as compared to the use of a single mode fiber. Further, as compared to a single mode fiber or waveguide, the aperture array disclosed herein may be more robust to dirt and hair. Additionally, the multi-aperture approach adopted in the aperture array can require less precise alignment between any given aperture and the optical receiver.

The features disclosed in the description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

All references referred to above are hereby incorporated by reference.

The invention claimed is:

1. A system, comprising:
 a wearable device, comprising an optical speckle receiver, the optical speckle receiver comprising:
 a single optical detector configured to capture a speckle pattern; and
 a plurality of apertures, or
 a plurality of lenses,
 wherein:
 each of the apertures or the lenses is adapted to receive a respective speckle signal from a respective discrete location of multiple discrete locations on a sample, and to transmit, from a respective terminal portion of the aperture or lens, the respective speckle signal onto the single optical detector, the respective terminal portions of the apertures or lenses being spatially separated from each other and configured such that respective speckle signals transmitted from two of the apertures or from two of the lenses at least partially spatially overlap on the optical detector, and
 the optical detector is configured to receive a respective speckle signal from each of the plurality of apertures or from each of the plurality of lenses.

2. The system of claim 1, wherein the sample is tissue.

3. The system of claim 1, wherein:
 the optical speckle receiver comprises a plurality of apertures; and
 an aperture of the plurality of apertures is a hole in a plate.

4. The system of claim 1, wherein:
 the optical speckle receiver comprises a plurality of apertures; and
 the apertures include a plurality of single mode or multi-mode fibers, each single mode or multi-mode fiber corresponding to a respective aperture of the plurality of apertures.

5. The system of claim 1, wherein:
 the optical speckle receiver comprises a plurality of lenses; and
 the lenses include a plurality of microlenses.

6. The system of claim 1, wherein:
the optical speckle receiver comprises a plurality of lenses; and
the plurality of lenses comprises individual lenses or a monolithic block of lenses.

7. The system of claim 1, wherein the distance between the plurality of apertures or the plurality of lenses and the optical detector is less than 5 cm.

8. The system of claim 1, wherein:
the optical speckle receiver comprises a plurality of lenses; and
the lenses are spherical, aspherical, or cylindrical.

9. The system of claim 1, wherein the optical detector is a photodiode, an array of photodiodes, a pixel array, or an image sensor.

10. The system of claim 1, wherein the wearable device comprises an optical transceiver comprising:
the optical speckle receiver; and
a coherent light source.

11. The system of claim 10, wherein the coherent light source operates at one or more ultraviolet to infrared (IR) wavelengths.

12. The system of claim 10, wherein the coherent light source includes a coherent light source operating at one or more visible wavelengths.

13. The system of claim 10, wherein the optical transceiver is arranged in a reflection mode such that light from the coherent light source produces speckle via multiple pathlength travel in the sample, and the apertures or the lenses are placed to receive speckle from the sample and to pass this light to the optical detector.

14. The system of claim 10, wherein the optical transceiver is arranged in a transmission mode, such that light from the coherent light source produces speckle via multiple pathlength travel in the sample, the apertures or the lenses being positioned to receive light transmitted through the sample and to pass this light to the optical detector.

15. The system of claim 1, wherein the apertures or the lenses form a portion of an outer casing of the wearable device.

16. The system of claim 1, wherein the wearable device has a size and dimension to be worn on an ear, toe, finger, wrist, chest, or upper arm.

17. The system of claim 16, wherein the wearable device has a size and dimension to be worn on a wrist.

18. The system of claim 1, wherein the optical detector is a photodiode array or a pixel array.

19. A plurality of apertures or a plurality of lenses, configured to be located in-between tissue and a single optical detector such that:
each of the apertures or the lenses receives a speckle signal from a respective discrete location of multiple discrete locations on the tissue, and transmits the respective speckle signal onto the single optical detector such that at least two of the speckle signals respectively transmitted onto the single optical detector from at least two of the apertures or from at least two of the lenses are partially spatially overlapping and partially spatially non-overlapping on the single optical detector, and
the optical detector receives a respective speckle signal from each of the plurality of apertures or from each of the plurality of lenses.

20. A system, comprising:
a wearable device, comprising an optical speckle receiver, the optical speckle receiver comprising:
an optical detector configured to capture a speckle pattern;
a plurality of apertures, or
a plurality of lenses; and
a free propagation region between the optical detector and the apertures or the lenses,
wherein:
each of the apertures or the lenses is adapted to receive a respective speckle signal from a respective discrete location of multiple discrete locations on a sample, and
the distance between the plurality of apertures or the plurality of lenses and the optical detector is less than 5 cm.

21. The system of claim 20, wherein the distance between the plurality of apertures or the plurality of lenses and the optical detector is less than 2 cm.

* * * * *